(12) United States Patent
Li et al.

(10) Patent No.: US 11,346,763 B2
(45) Date of Patent: May 31, 2022

(54) APPARATUS AND METHOD FOR MICROBIAL CELL COUNTING

(71) Applicant: Jiangnan University, Wuxi (CN)

(72) Inventors: Gongxin Li, Wuxi (CN); Fei Liu, Wuxi (CN); Xiaoli Luan, Wuxi (CN); Zhiguo Wang, Wuxi (CN); Jun Chen, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 17/139,113

(22) Filed: Dec. 31, 2020

(65) Prior Publication Data

US 2021/0123853 A1   Apr. 29, 2021

Related U.S. Application Data

(63) Continuation of application No. PCT/CN2020/090415, filed on May 15, 2020.

(30) Foreign Application Priority Data

Dec. 18, 2019   (CN) .......................... 201911309633.X

(51) Int. Cl.
    *G01N 15/14*   (2006.01)
    *G01N 33/487*  (2006.01)
    *G01N 15/00*   (2006.01)

(52) U.S. Cl.
    CPC ..... *G01N 15/1436* (2013.01); *G01N 15/1484* (2013.01); *G01N 33/48735* (2013.01); *G01N 2015/0065* (2013.01); *G01N 2015/1486* (2013.01)

(58) Field of Classification Search
    CPC .......... G01N 15/1436; G01N 15/1484; G01N 33/48735; G01N 2015/0065; G01N 2015/1486; G01N 2015/1493; G01N 15/1459; G01N 2015/1006
    See application file for complete search history.

(56) References Cited

U.S. PATENT DOCUMENTS

2008/0130093 A1   6/2008  Silberberg et al.
2017/0089823 A1*  3/2017  Wagner ................. G01N 21/65

FOREIGN PATENT DOCUMENTS

| CN | 102621117 A | 8/2012 |
|---|---|---|
| CN | 104745452 A | 7/2015 |
| CN | 110846217 A | 2/2020 |

(Continued)

*Primary Examiner* — Roy M Punnoose
(74) *Attorney, Agent, or Firm* — IPro, PLLC

(57) ABSTRACT

The disclosure discloses an apparatus and a method for microbial cell counting, and belongs to the field of cell counting. In the present application, by converting a traditional automated intermittent counting process into a continuous counting process, the cell sap fixed in a blood cell plate in a traditional counter becomes the cell sap flowing in a microchannel, so as to prolong the cell detection time and distance. The size of the microchannel is slightly greater than the diameter of microbial cells, so as to ensure that the cells flow through the cross section of the microchannel one by one. At the same time, since the diameter of the counterbores communicated by the microchannel is slightly greater than the width of the microchannel, the flow rate of the cell sap slows down when the cell sap flows to the counterbores.

13 Claims, 7 Drawing Sheets

(56) References Cited

FOREIGN PATENT DOCUMENTS

| DE | 102008049878 A1 | * | 4/2010 | ......... G02B 21/0032 |
|---|---|---|---|---|
| DE | 102010012580 A1 | * | 9/2011 | ......... G01N 21/6408 |
| WO | 2016161337 A1 | | 10/2016 | |
| WO | 2019226897 A2 | | 11/2019 | |
| WO | WO-2019213166 A1 | * | 11/2019 | ............. A61B 5/145 |

\* cited by examiner

IMA: 0.000 mm

APPARATUS AND METHOD FOR MICROBIAL CELL COUNTING

TECHNICAL FIELD

The disclosure relates to an apparatus and a method for microbial cell counting, and belongs to the field of cell counting.

BACKGROUND

Microbial fermentation industry is an important component and foundation of biotechnology, and plays an increasing role in modern food, energy, medicine and other high value-added industries. The essence of microbial fermentation is a process of preparing microbial thalli, direct metabolites or secondary metabolites by means of microbial cell communities. The function of microbial cells needs to work together in the form of microbial communities, and therefore, the number or concentration of the microbial cells directly affects the efficiency of microbial fermentation.

The traditional technology has the following technical problems:

Achieving accurate counting of the microbial cells plays vital roles in research of the microbial cells and improvement of the fermentation efficiency. At present, methods for counting microbial cells can be classified into two categories: a manual microscope counting method and an automatic blood cell counting method.

The manual microscope counting method is to firstly dilute cell samples appropriately, fill the cell samples into a cell counting pool, count the number of cells in a certain volume of a counting plate under a microscope, and calculate the number of cells per liter of the samples by conversion. This method is a purely manual counting method which is larger in counting error and is time-consuming and labor-consuming.

The automatic blood cell counting method is to uniformly mix the cell suspension and drop the cell suspension on a blood cell plate, and then insert the cell plate into a cell counter which can automatically complete the cell counting. At present, according to the principle, cell counters can be divided into: methods based on image processing, methods based on spectroscopy and methods based on immunology. The method based on images detects sample cell contours in the blood cell suspension through an image recognition method, then counts the detected cell contours, and converts them into cell concentration. Cell counters based on the image recognition method have relatively mature products at home and abroad, such as Countess II series counters produced by ThermoFisher company. However, counters based on the image processing methods are prone to larger counting errors when there are cell agglomerations or more impurities in the suspension. The method based on spectroscopy calculates the intensity difference of the spectrum projected on the cell sap, and then deduces the cell concentration. This method actually obtains the statistical value of the cell communities in the cell suspension, and there are still errors caused by the existence of cell residues and the like in the cell sap that cannot be ruled out. After staining the cells with reagents such as trypan blue for cell counting based on an immunological method, the number of the cells is calculated by a fluorescence detection method. This method has the obvious defects that it is necessary to stain the cells, the sample processing is complicated, and the cells are damaged.

SUMMARY

In order to solve the problem of larger errors in the current viable cell counting method and realize accurate counting of microbial cells without damaging the cells, the disclosure provides an apparatus and a method for microbial cell counting. By changing the traditional automated intermittent counting process of cells into a continuous process, the disclosure not only effectively improves the cell counting accuracy, but also can realize accurate statistics of cell size distribution.

In one aspect, the present application provides an apparatus for microbial cell counting. The apparatus includes a DMD (Digital Micromirror Device) module, a transparent channel chip module, a light path module, a detection and analysis module and an installation supporting module. The DMD module, the transparent channel chip module, the light path module and the detection and analysis module are sequentially installed on the installation supporting module.

The transparent channel chip module is provided with a microchannel, and the width of the microchannel is adapted to the diameter of the cells in the liquid, so that the cells can circulate one by one in the microchannel.

The DMD module is provided with a DMD, and the turning direction of each micromirror in the DMD is adjustable.

When the apparatus is used to count the cells in the liquid, the liquid circulates through the microchannel in the transparent channel chip module, at the same time, detection light is used to irradiate the transparent channel chip module, the detection light passes through the transparent channel chip module in a forward direction and then irradiates the DMD module, is reflected by the DMD in the DMD module, then passes through the transparent channel chip module in a reverse direction, and then is adjusted by the light path module to reach the detection and analysis module, and the detection and analysis module calculates the number and size of the cells in the liquid according to the light intensity change of the detection light.

Optionally, the transparent channel chip module includes a microchannel plate made of a transparent material; the microchannel is a groove with a rectangular cross section formed in the microchannel plate; and the microchannel plate is further provided with counterbores arranged corresponding to the DMD in the DMD module, the microchannel is communicated with all the counterbores, and the diameter of the counterbores is greater than the width of the microchannel.

Optionally, the DMD module further includes a DMD control plate, and the DMD control plate is configured to control each micromirror in the DMD to turn in direction according to a certain rule.

Optionally, the cross section of the microchannel is square, the side length is 5-7 μm, and the diameter of the counterbores is 7-10 μm.

Optionally, the light path module includes a detection light source, a beam splitter, a plano-concave lens, plano-convex lenses and a focusing objective lens. The light path module is configured to ensure that the detection light emitted by the detection light source is amplified by one plano-convex lens and then vertically irradiates the transparent channel chip module through the beam splitter, passes through the transparent channel chip module in a forward direction and then irradiates the DMD module, is reflected by the DMD in the DMD module and then passes through the transparent channel chip module in a reverse direction, passes through the beam splitter, then sequentially passes through one plano-convex lens and the plano-concave lens to reach the focusing objective lens, and then is converged on a detection device in the detection and analysis module by the focusing objective lens.

Optionally, the transparent channel chip module further includes a chip fixing frame, a channel fixing frame and a channel cover sheet.

The chip fixing frame is connected to the DMD module, and is configured to fix the microchannel plate above the DMD in the DMD module; a sinking through hole is formed in the center position of the chip fixing frame, and the microchannel plate, the channel cover sheet and the channel fixing frame are sequentially placed in the through hole.

The channel fixing frame is configured to fix the channel cover sheet and the microchannel plate on the chip fixing frame.

The channel cover sheet is made of a transparent material, and is configured to cover the microchannel plate to prevent the liquid circulating in the microchannel from being contaminated.

Optionally, the transparent channel chip module further includes two liquid pipelines and a pump. The two liquid pipelines are respectively connected to an inlet and an outlet of the microchannel. The other end of the liquid pipeline connected to the inlet of the microchannel is connected with the pump, and the pump is configured to inject liquid into the microchannel, so that the liquid circulates through the microchannel.

Optionally, the inlet and the outlet of the microchannel are respectively provided with a rectangular groove, and the size of the rectangular groove is 50 μm×50 μm×7 μm.

Optionally, the detection and analysis module includes a light detection device, a PC (Personal Computer) and analysis software. The detection and analysis module is configured to obtain the light intensity data of the detection light reaching the light detection device, and analyze a cell number and cell size distribution diagram through the analysis software according to the light intensity data.

In another aspect, the present application further provides a method for microbial cell counting. The method uses the above apparatus for microbial cell counting, and the method includes:

injecting a cell suspension into the microchannel, using detection light to irradiate the transparent channel chip module during the flow of the cell suspension in the microchannel; enabling the detection light to pass through the transparent channel chip module in a forward direction and then irradiate the DMD module, be reflected by the DMD in the DMD module and then pass through the transparent channel chip module in a reverse direction, and then be adjusted by the light path module to reach the detection and analysis module; calculating the number and size of the cells in the liquid by the detection and analysis module according to the light intensity change of the detection light; and enabling each micromirror in the DMD in the DMD module to turn in direction according to a certain rule during counting, so as to adjust the light intensity detected by the detection and analysis module.

Optionally, the DMD module uses the Discovery series of a DLP chip, and each micromirror in the DMD in the DMD module turns according to the rule set by the DLP chip.

Optionally, the light intensity of the detection light is represented by current.

Optionally, the method includes:

setting the flow rate of the cell suspension as V, the cross-sectional area of the microchannel as s, the sampling time as T, the sampling rate as C, and the difference between the current signal detected at the ith site at the time t and the reference current value as $\Delta I_i(t)$, wherein the reference current value is the current value when pure liquid flows through;

defining the number of cells at a single sampling point at the ith site as:

$$P_i = n(I^*_{n+1} > \Delta I_i(t) \geq I^*_n)$$

wherein n is an integer, $I^*_i$ corresponds to the reference value of the current value difference of i cells, the cell concentration is $$C = \frac{c}{vsk} \sum_k P_i,$$

and k is the number of detection sites; and letting $k_d$ represent the cell diameter corresponding to the reference value of the unit current difference, obtaining the cell diameter $$D_i(t) = k_d \frac{\Delta I_i(t)}{P_i}$$

sampled at the ith site at the time t, obtaining a mean value based on the cell diameter obtained at each site, and then drawing a cell size distribution diagram.

The present application further provides a computer device, including a memory, a processor and a computer program stored in the memory and capable of running on the processor, wherein when the processor performs the computer program, the steps in the above method are implemented.

The disclosure has the following beneficial effects:

In the disclosure, by converting the traditional automated intermittent counting process into a continuous counting process, the cell sap fixed in a blood cell plate in a traditional counter becomes the cell sap flowing in the microchannel of the disclosure, so as to prolong the cell detection time and distance. The size of the microchannel is slightly greater than the diameter of the microbial cells, so as to ensure that the cells flow through the cross section of the microchannel one by one during circulating. At the same time, since the diameter of the counterbores communicated by the microchannel is slightly greater than the width of the microchannel, the flow rate of the cell sap slows down when the cell sap flows to the counterbores. On the one hand, it is more conducive to the detection of the size and number of the cells. On the other hand, the impurities in the cell sap can be separated from the cells, so as to avoid errors caused by the impurities. In addition, by controlling the turning process of the micromirror in the DMD, the cell condition in each "grid" of the channel can be detected in time to realize accurate cell counting, and the size of each cell can be detected in real time to provide a detected cell size distribution diagram. Because the cell size distribution can reflect the cell growth level and overall cell quality to a certain extent, the cell size distribution diagram obtained in the present application plays vital roles in selection of excellent microbial strains and improvement of microbial production efficiency.

BRIEF DESCRIPTION OF FIGURES

In order to more clearly illustrate the technical schemes of the examples of the disclosure, the accompanying drawings used in the description of the examples are briefly described below. It is obvious that the accompanying drawings in the following description are only some examples of the disclosure, and other accompanying drawings are obtained by those skilled in the art based on these accompanying drawings without any creative effort.

DETAILED DESCRIPTION

In order to make the objectives, technical schemes and advantages of the disclosure clearer, the examples of the disclosure will be further described in detail below with reference to the accompanying drawings.

Figure 1:
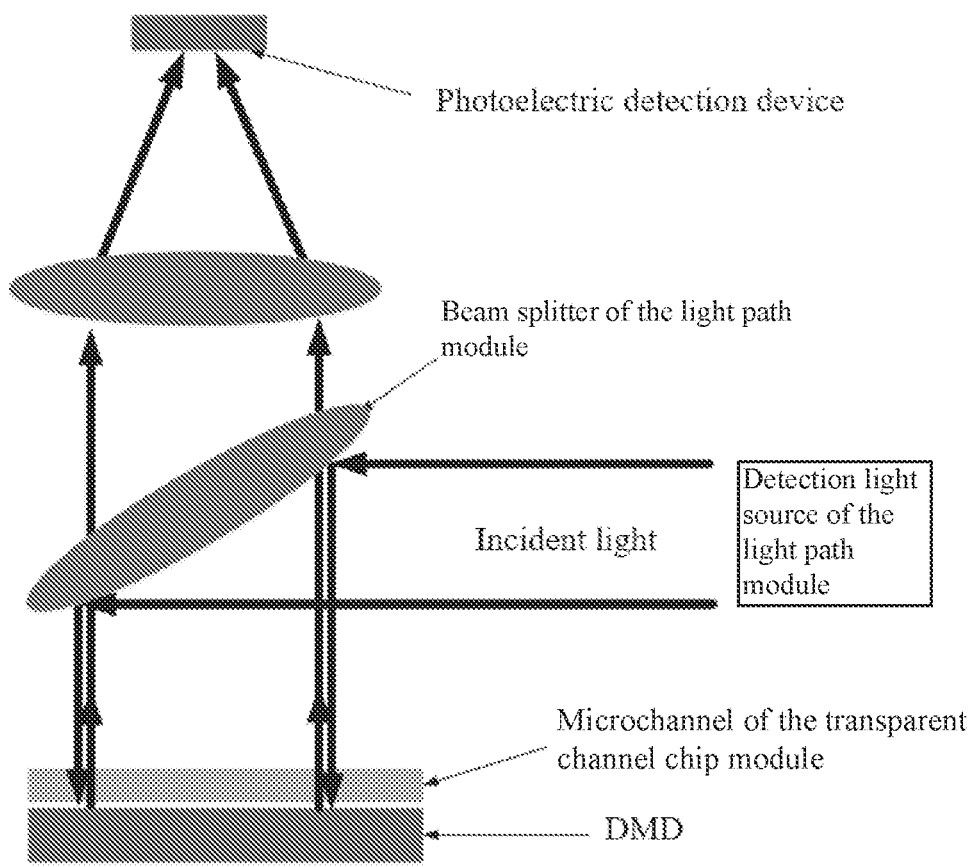
FIG. 1 is a principle diagram of a method for microbial cell counting of the disclosure.

The disclosure provides an accurate apparatus and a method for microbial cell counting based on a digital micromirror array (DMD) and a microchannel. The basic principle is shown in FIG. 1. A DMD is placed in parallel below the microchannel, the cell suspension circulates in the microchannel, the detection light irradiates the cell suspension circulating in the microchannel, the light intensity of the detection light changes due to the existence of cells, and the detection light passes through the microchannel and then irradiates each micromirror in the DMD, is reflected to irradiate the cell suspension circulating in the microchannel again, passes through the microchannel again, and then is converged on a photoelectric detection device by a series of optical devices. During counting, each micromirror in the DMD is controlled to turn according to a rule, and then the light intensity (represented by current) is converted into the cell number and the cell size by calculating and counting the light intensity on the photoelectric detection device, so as to draw a cell size distribution diagram. The method changes the traditional intermittent counting process of cells into a continuous process. By injecting the cell suspension into the microchannel, the cell suspension is continuously counted through an optical detection method during the flow in the microchannel. The diameter of the microchannel is similar to the diameter of the cells, which ensures that the cells circulate one by one in the channel to realize accurate cell counting, and the size of each cell can be detected in real time to give a detected cell size distribution diagram.

Example 1

The present example provides an apparatus for microbial cell counting. The apparatus includes a DMD module, a transparent channel chip module, a light path module, a detection and analysis module and an installation supporting module. The DMD module, the transparent channel chip module, the light path module and the detection and analysis module are sequentially installed on the installation supporting module.

The transparent channel chip module is provided with a microchannel, and the width of the microchannel is adapted to the diameter of the cells in the liquid, so that the cells can circulate one by one in the microchannel.

The DMD module is provided with a DMD, and the turning direction of each micromirror in the DMD is adjustable.

When the apparatus is used to count the cells in the liquid, the liquid circulates through the microchannel in the transparent channel chip module, at the same time, detection light is used to irradiate the transparent channel chip module, the detection light passes through the transparent channel chip module in a forward direction and then irradiates the DMD module, is reflected by the DMD in the DMD module, then passes through the transparent channel chip module in a reverse direction, and then is adjusted by the light path module to reach the detection and analysis module, and the detection and analysis module calculates the number and size of the cells in the liquid according to the light intensity change of the detection light.

The transparent channel chip module includes a microchannel plate made of a transparent material; the microchannel is a groove with a rectangular cross section formed in the microchannel plate; and the microchannel plate is further provided with counterbores arranged corresponding to the DMD in the DMD module, the microchannel is communicated with all the counterbores, and the diameter of the counterbores is greater than the width of the microchannel.

The DMD module further includes a DMD control plate, and the DMD control plate is configured to control each micromirror in the DMD to turn in direction according to a certain rule.

Figure 2A:
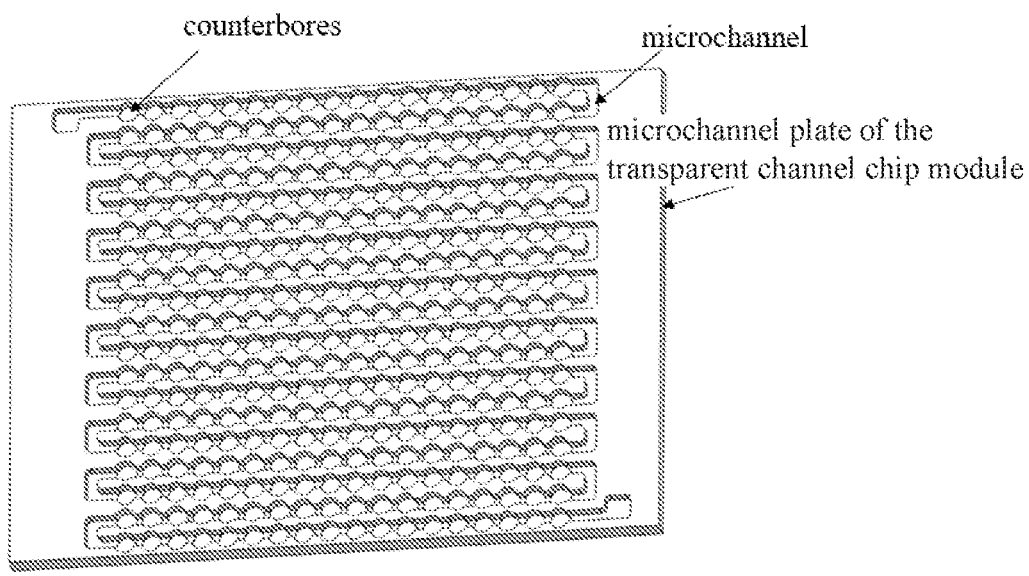
FIG. 2A is a schematic diagram of a microchannel in an apparatus for microbial cell counting in an example of the disclosure.

Specifically, the microchannel in the present application is a channel communicated with a "grid" array processed on a microchannel plate by using a photoetching technology, as shown in FIG. 2A. Each "grid" has a straight side length of 13.7 μm and contains a round hole, that is, a counterbore communicated with the microchannel, of which the diameter is about 7 μm; the width of the non-"grid" region of the entire channel is about 5 μm, and the channel is communicated with all the round holes in the "grid"; and the front and rear ends of the channel are respectively communicated with a square groove with the diameter of about 50 μm×50 μm×7 μm, which is used for the inflow and outflow of cell sap.

Figure 2B:
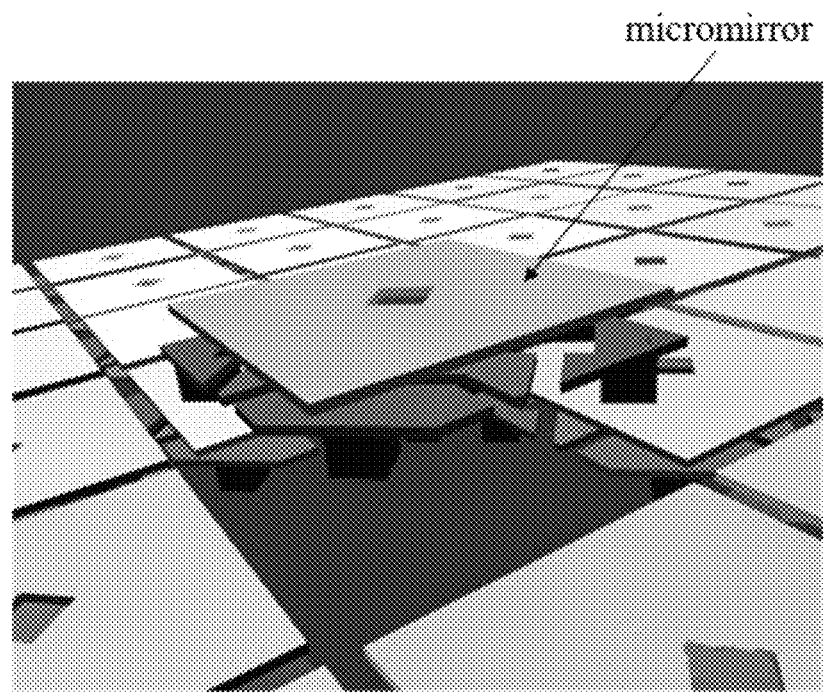
FIG. 2B is a structure diagram of a DMD in an apparatus for microbial cell counting in an example of the disclosure.

The DMD is a micromirror array composed of a series of micromirrors. As shown in FIG. 2B, the surface of each micromirror is a smooth mirror surface, which has a higher reflectivity for light in a specific wavelength range. Each micromirror has a side length of 13.7 μm, and can be turned by 12° to both sides along the diagonal of the micromirror. The DMD control plate can accurately and quickly control the turning direction of each micromirror, so as to adjust the position or shape of the reflected light on the DMD.

Figure 2C:
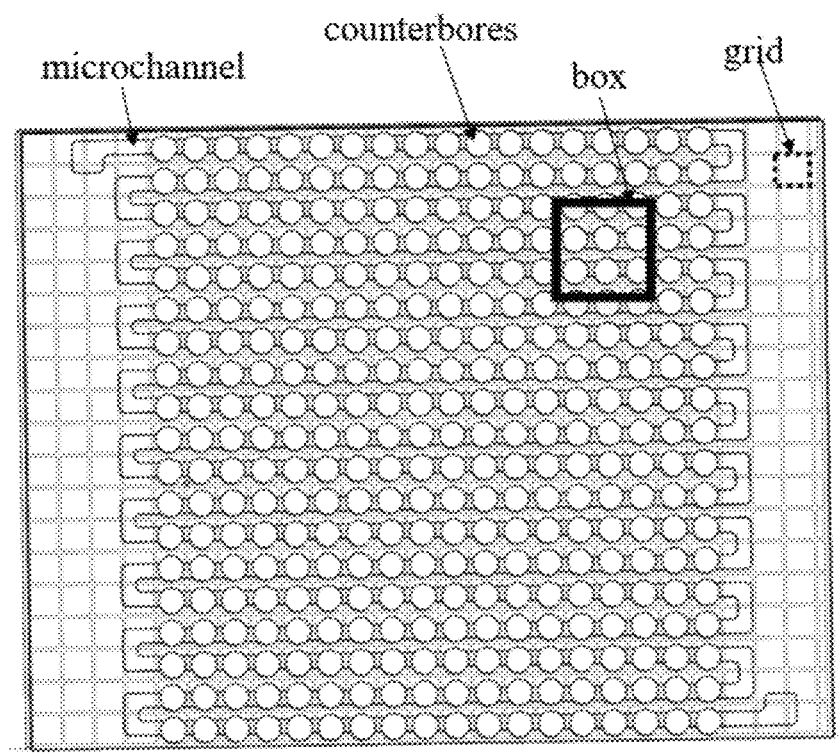
FIG. 2C is a diagram of position relationship between a microchannel and a DMD in an apparatus for microbial cell counting in an example of the disclosure.
Figure 2D:
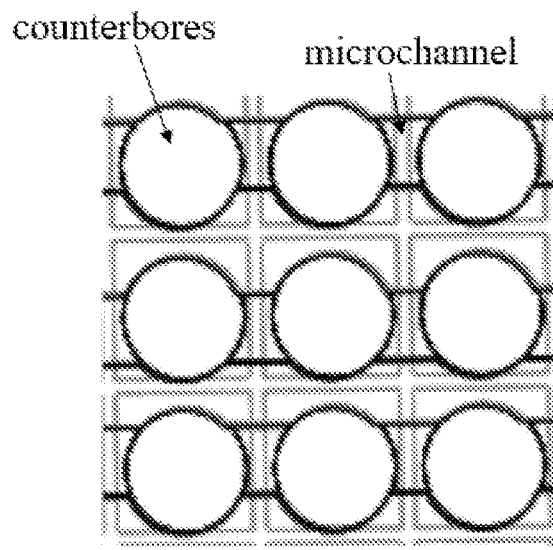
FIG. 2D is an enlarged diagram in a box of FIG. 2C.

The microchannel is placed right above the DMD, and each "grid" is aligned with one micromirror of the DMD, as shown in FIG. 2C and FIG. 2D. The light is incident on the DMD vertically, and the micromirror placed in the horizontal position in the DMD can reflect the light back in a vertical upward direction (as shown in FIG. 1). By accurately controlling the turning direction of each micromirror, the intensity of the light reflected by the corresponding micromirror is converted into the number and size of the cells in the round hole above the micromirror.

Example 2

Figure 3:
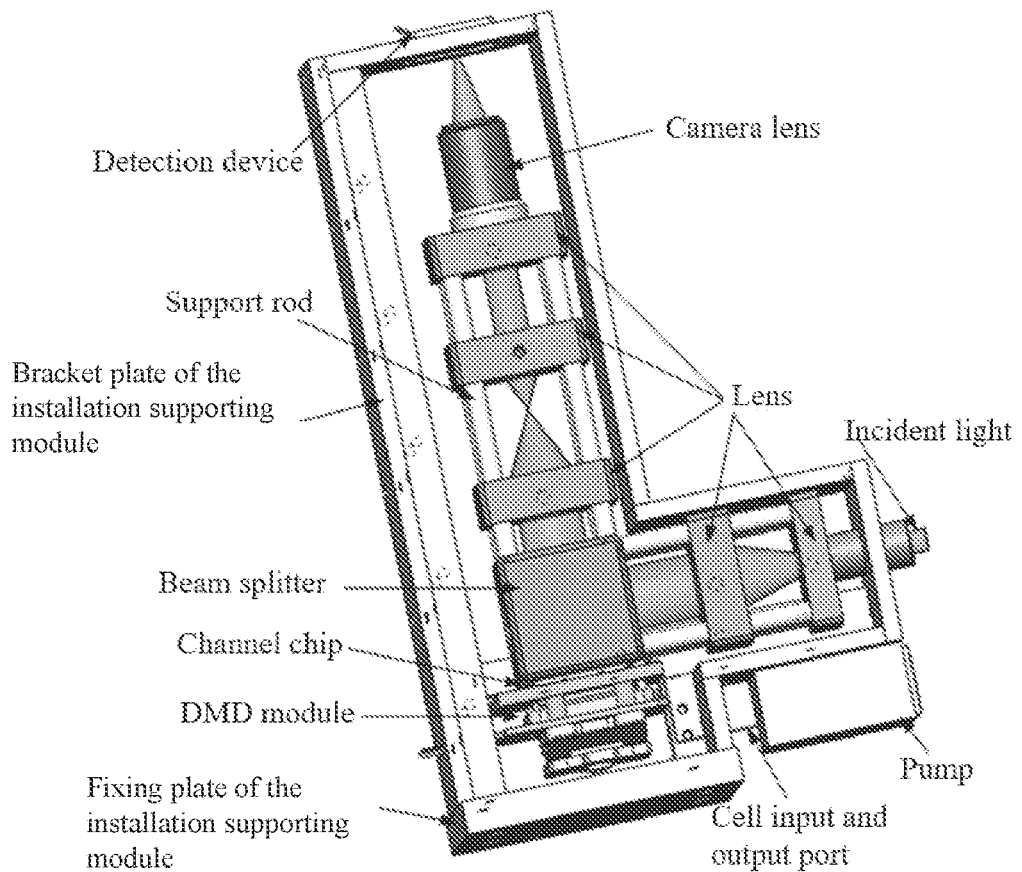
FIG. 3 is a structure diagram of an apparatus for microbial cell counting in an example of the disclosure.

The present example provides an apparatus for microbial cell counting, as shown in FIG. 3. The apparatus mainly includes a transparent channel chip module, a DMD module, a light path module, a detection and analysis module and an installation supporting module.

The channel chip module is directly fixed right above the DMD module; the light path module is fixed above the channel chip module; the detection and analysis module is placed at the convergence position of the outlet light above the light path module; and the installation supporting module fixes all the modules according to the above position sequence.

Figure 4:
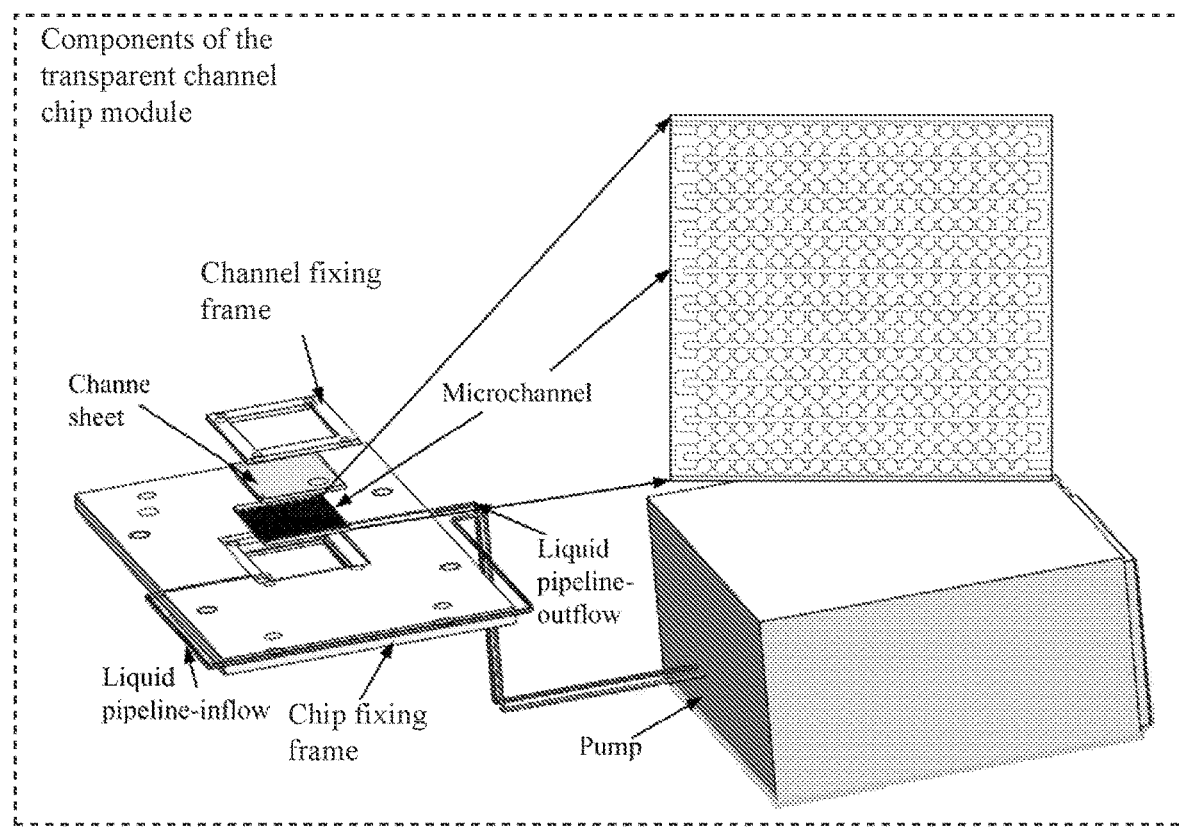
FIG. 4 is a schematic diagram of a transparent channel chip module in an apparatus for microbial cell counting in an example of the disclosure.

As shown in FIG. 4, the transparent channel chip module includes a chip fixing frame, a microchannel plate, a channel cover sheet, a channel fixing frame, a pump and two liquid pipelines, and the two liquid pipelines are respectively a "liquid pipeline-inflow" and a "liquid pipeline-outflow".

The chip fixing frame is connected to the DMD module, and is mainly configured to fix the channel at a suitable position above the DMD.

A sinking square through hole is formed in the center position of the chip fixing frame, and the microchannel plate, the channel cover sheet and the channel fixing frame are sequentially placed in the hole.

The two liquid pipelines are respectively configured to inject cell sap from the outside into the channel and to enable the cell sap to flow out of the channel. One end of the "liquid pipeline-inflow" passes through the channel fixing frame and the channel cover sheet and goes deep into the inflow port of the microchannel, and the other end of the "liquid pipeline-inflow" is connected to the output port of the pump, and the pump is configured to inject the liquid into the microchannel, so that the liquid circulates through the microchannel. One end of the "liquid pipeline-outflow" passes through the channel fixing frame and the channel cover sheet and goes deep into the outflow port of the microchannel, and the other end of the "liquid pipeline-outflow" can be connected to another container for containing cell sap, so that the cell sap flowing through the microchannel is stored in a concentrated manner.

Figure 5:
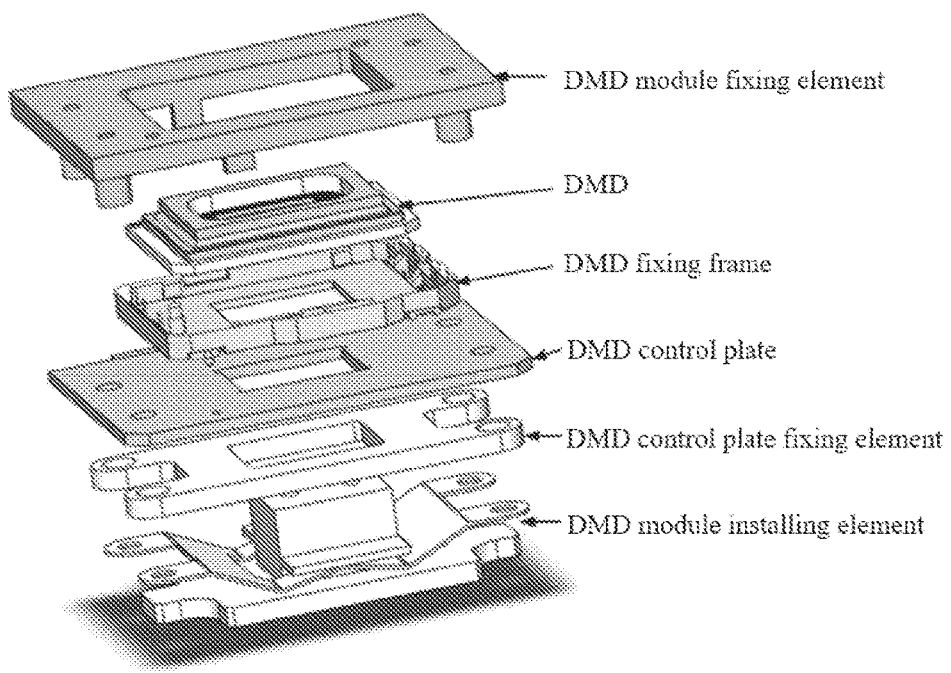
FIG. 5 is a structural diagram of a DMD module in an apparatus for microbial cell counting in an example of the disclosure.

As shown in FIG. 5, the DMD module mainly includes a DMD chip, a DMD control plate and corresponding fixing frames. The DMD chip is composed of a micromirror array and corresponding control circuit and package thereof as shown in FIG. 2B. The DMD control plate is configured to control the turning of the micromirror in the DMD chip. The fixing frames are configured to connect the DMD chip and the DMD control plate, connect the DMD module and the microchannel chip, and fix the DMD module on the installation supporting module of the apparatus.

Figure 6:
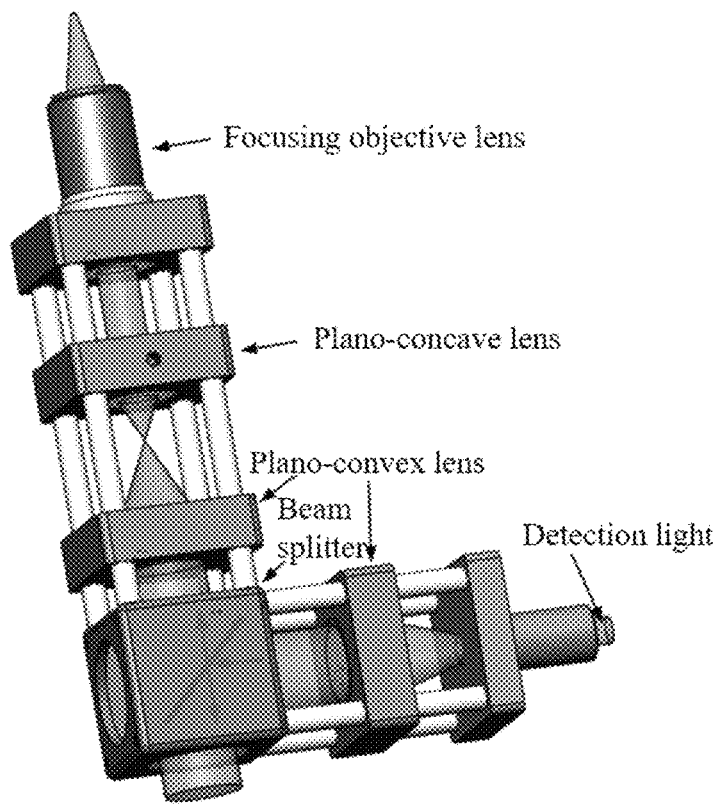
FIG. 6 is a schematic diagram of a light path module in an apparatus for microbial cell counting in an example of the disclosure.

The light path module mainly includes a series of lenses, corresponding installation cage plates, a focusing objective lens, a detection light source and corresponding cage plate support rods. Specifically, as shown in FIG. 6, a series of lenses include two plano-convex lenses, a plano-concave lens and a focusing objective lens, and the focusing objective lens is a lens. The optical module is configured to realize that the incident detection light is amplified and then vertically irradiates the DMD through the beam splitter, then is reflected by the DMD, sequentially passes through the beam splitter, the set of lenses and a camera lens, and is converged on the light detection device in the detection and analysis module. As shown in FIG. 6, the set of lenses include a plano-convex lens and a plano-concave lens. The set of lenses reduce the parallel incident light and then output the light to the inlet of the camera lens in parallel, and the camera lens is a camera lens of the focusing objective lens.

The detection and analysis module mainly includes a light detection device, a PC, analysis software and the like, and is configured to detect the light reflected by the DMD in a vertical direction, and analyze a cell number and cell size distribution diagram through the analysis software based on the detection data.

The installation supporting module is mainly configured to support and fix other modules.

The microchannel in the transparent channel chip module has an effect of changing the traditional intermittent counting process of cells into a continuous process, so that the cell sap flows through the microchannel one by one.

The microchannel in the present application can be processed on transparent tempered glass (that is, a microchannel plate) by a photoetching method, and includes 768×768 "grids". Each "grid" is a square with a side length of 13.7 μm; a round hole with the diameter of 7 μm is formed in the center; the hole depth is 7 μm; all the holes are communicated by a channel with the cross section of 5 μm×5 μm; and two adjacent rows of the channel are connected end to end. An inlet and an outlet of the channel are positioned in a diagonal of the channel plate and are directly communicated with the channel to realize the injection and outflow of the cell sap, and the sizes of the inlet and the outlet are both 50 μm×50 μm×7 μm.

The design of the channel chip module is shown in FIG. 4. The module is mainly composed of a chip fixing frame, a microchannel (formed in the microchannel plate), a channel cover sheet, a channel fixing frame, liquid pipelines and a pump.

The chip fixing frame is connected to the DMD module, and is configured to fix the microchannel plate at a suitable position above the DMD in the DMD module (here, the "suitable position" can be set by those skilled in the art according to the common knowledge in the field and considering the overall mechanical structure of the device); a sinking through hole is formed in the center position of the chip fixing frame, and the microchannel plate, the channel cover sheet and the channel fixing frame are sequentially placed in the through hole.

The channel fixing frame is configured to fix the channel cover sheet and the microchannel plate on the chip fixing frame.

The channel cover sheet is made of a transparent material, and is configured to cover the microchannel plate to prevent the liquid circulating in the microchannel from being contaminated.

Specifically, a sinking square through hole is formed in the middle of the chip fixing frame, and the edges of the chip fixing frame are provided with threaded counterbores and pipeline grooves for installing and fixing. The microchannel plate is directly installed in the sinking square through hole in the middle of the chip fixing frame, and the channel cover sheet and the channel fixing frame are placed upwards in sequence. The upper surface of the channel fixing frame is flush with the upper surface of the chip fixing frame, and four screw counterbores are formed around the channel fixing frame so as to fix the microchannel plate on the chip fixing frame. The channel cover sheet is made of a single-layer glass sheet, and the surface size of the channel cover sheet is equal to the size of the microchannel plate. Two symmetrical holes are formed in one of the diagonals of the channel cover sheet, and the center positions of the holes respectively correspond to the centers of the inlet and the outlet of the microchannel. The channel fixing frame and the chip fixing frame can be processed by aluminum materials. The two liquid pipelines are hoses with the diameter of 1/16 inch, and are respectively connected with the inlet and the outlet of the microchannel, wherein the other end of the liquid pipeline for inflow is connected with the inlet of the pump.

In practical applications, the DMD module directly uses the Discovery series of a DLP (Digital Light Procession) chip. The DMD type is 0.7-inch VGA series, including 1024×768 digital micromirrors, and each micromirror is a square with the side length of 13.7 μm and is suitable for all wave bands from ultraviolet to near infrared. The refresh rate of a control plate is up to 290 Hz.

The specific structure of the DMD module is shown in FIG. 5. From top to bottom, there are a DMD module fixing frame, a DMD chip, a DMD fixing frame, a DMD control plate, a DMD control plate fixing frame and a DMD module installing element in sequence. Four symmetrical screw holes in both sides of the DMD module fixing frame are connected to the DMD control plate, the DMD control plate fixing frame and the DMD module installing element, so as to fix the DMD and the DMD control plate. For how the DMD control plate controls the turning of each micromirror in the DMD, please refer to the relevant instructions of the Discovery series of the DLP chip, which will not be repeated here.

Specifically, each micromirror in the DMD can be turned by 10° in two directions along a hinge on the diagonal, each micromirror can be turned in a specific direction by controlling the switching-on and switching-off of the two circuits of the hinge, and the switching-on and switching-off information of the circuits is input through a DLP control system. During counting, all micromirrors are turned by 10° in the same direction, and then the micromirrors are controlled to quickly turn back to the horizontal direction one by one in sequence according to the liquid flow direction. The detection light can only be reflected on the photoelectric detection device after passing through the micromirror in the horizontal direction.

Figure 8A:
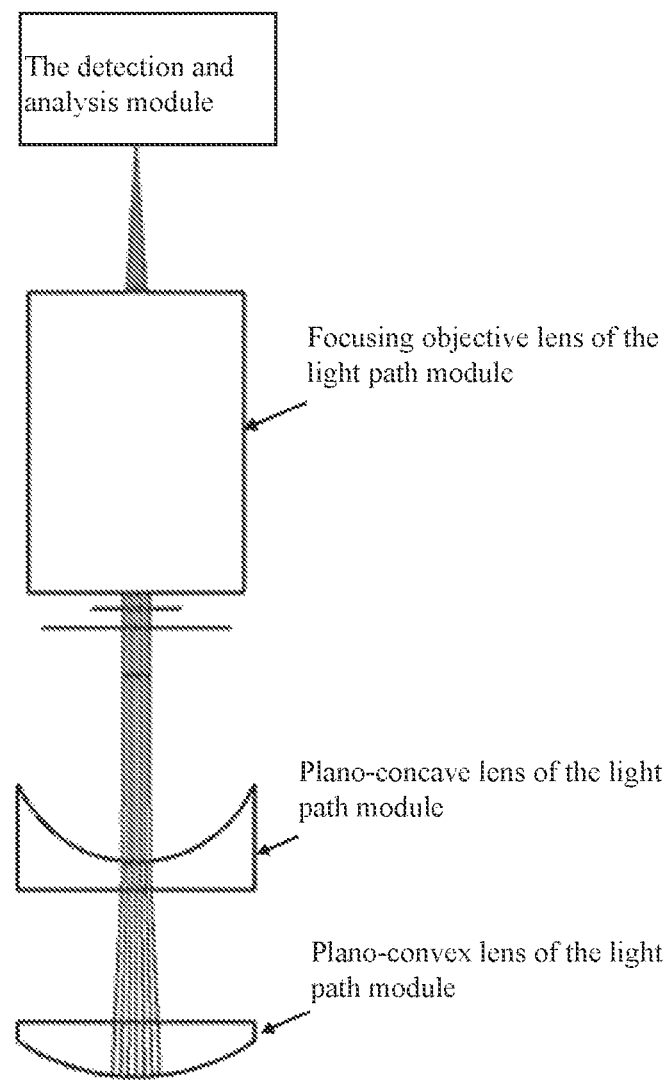
FIG. 8A is a two-dimensional light path diagram of a radiation light path in an apparatus for microbial cell counting in an example of the disclosure.
Figure 8B:
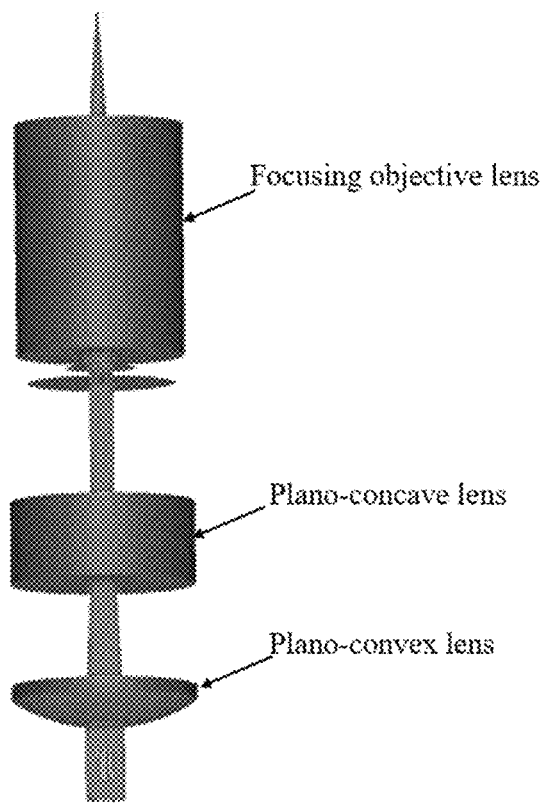
FIG. 8B is a three-dimensional light path diagram of a radiation light path in an apparatus for microbial cell counting in an example of the disclosure.
Figure 8C:
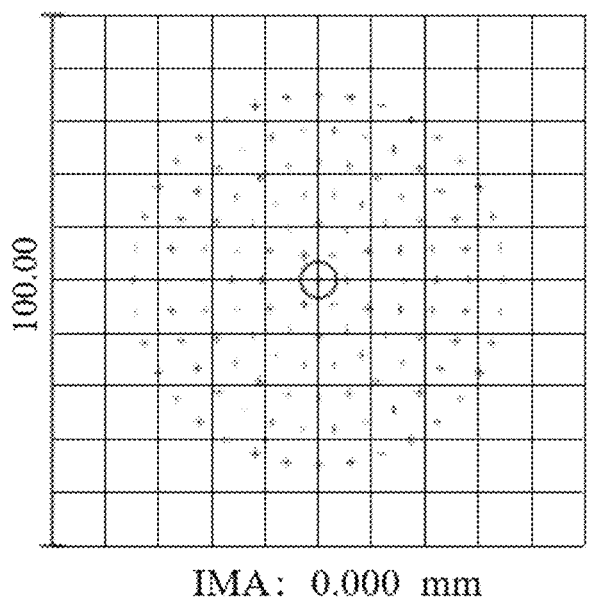
FIG. 8C is a focus point information diagram of a radiation light path in an apparatus for microbial cell counting in an example of the disclosure.

The design of the light path module is shown in FIG. 6. The entire light path module is built with a 30 mm standard cage plate system. The detection light is emitted by a laser device with better parallelism (not shown in the figure), and is amplified by a plano-convex lens and then vertically irradiates the mirror surface of the DMD through the beam splitter; and the light reflected by the mirror surface of the DMD passes through the beam splitter and then respectively passes through a plano-convex lens and a plano-concave lens, so that the light beam is reduced and enters a 10-fold focusing objective lens in parallel. FIG. 8A and FIG. 8B are respectively a two-dimensional simulated light path diagram and a three-dimensional simulated light path diagram of a reflected light path. After the parallel incident light beam with the diameter of 5 mm is reduced by the plano-convex lens and the plano-concave lens, the diameter of the light beam is reduced to 3.3 mm, and the light beam still maintains good parallelism, as shown in FIG. 8C; and the light beam is reduced by the focusing objective lens and then converged on the detection device above the objective lens.

Figure 7:
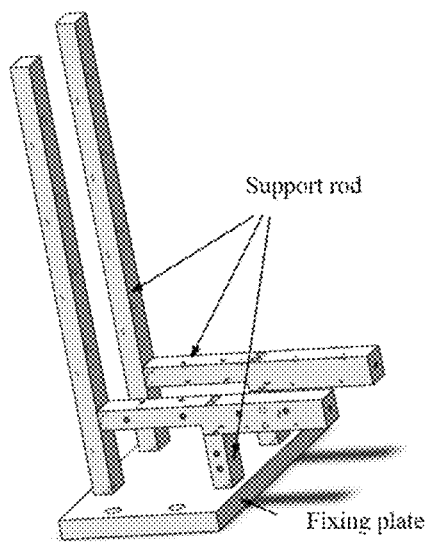
FIG. 7 is a schematic diagram of an installation frame in an apparatus for microbial cell counting in an example of the disclosure.

An apparatus installation frame is as shown in FIG. 7. The installation frame is mainly composed of support rods and a fixing plate and is configured to install an apparatus and fix other modules. The support rod is made of an aluminum material with the cross section of 10 mm×15 mm, and the fixing plate is made of an aluminum plate with the thickness of 10 mm.

Example 3

The present example provides a method for microbial cell counting. The method uses the above apparatus for microbial cell counting, and the method includes:

a cell suspension is injected into the microchannel; the detection light is used to irradiate the transparent channel chip module during the flow of the cell suspension in the microchannel; the detection light passes through the transparent channel chip module in a forward direction and then irradiates the DMD module, is reflected by the DMD in the DMD module, then passes through the transparent channel chip module in a reverse direction, and then is adjusted by the light path module to reach the detection and analysis module; the detection and analysis module calculates the number and size of the cells in the liquid according to the light intensity change of the detection light; and each micromirror in the DMD in the DMD module is turned in direction according to a certain rule during counting, so as to adjust the light intensity detected by the detection and analysis module.

The detection and analysis module uses a method of multi-site sampling and mean value calculation under constant flow when counting the number of cells and drawing a cell size distribution diagram. Each site is the position on the microchannel corresponding to each micromirror, that is, the "grid" on the microchannel corresponding to each micromirror. A specific calculation method is:

the flow rate of the pump is set as v, the cross-sectional area of the channel is set as s, the sampling time is set as T, the sampling rate is set as c, and the difference between the current signal detected at the ith site at the time t and the reference current value is set as $\Delta I_i(t)$; the number of cells at a single sampling point at the ith site is defined as: $P_i = n$ $(I^*_{n+1} > \Delta I_i(t) \geq I^*_n)$, wherein n is an integer and represents the number of cells, $I^*_i$ corresponds to the reference value of the current value difference of i cells, correspondingly, $I^*_n$ corresponds to the reference value of the current value difference of n cells, the cell concentration is $$C = \frac{c}{vsk} \sum_k P_i,$$

and k is the number of detection sites; and $k_d$ is set to represent the cell diameter corresponding to the reference value of the unit current difference, the cell diameter $$D_i(t) = k_d \frac{\Delta I_i(t)}{P_i}$$

sampled at the ith site at the time t is obtained, a mean value is obtained based on the cell diameter obtained at each site, and then a cell size distribution diagram is drawn.

Some of the steps in the examples of the disclosure may be implemented through software, and corresponding software programs may be stored in a readable storage medium, such as an optical disk or a hard disk.

The foregoing descriptions are merely preferred examples of the disclosure, and are not intended to limit the disclosure. Any modification, equivalent substitution, improvement and the like made within the spirit and principle of the disclosure shall fall within the protection scope of the disclosure.

What is claimed is:

1. An apparatus for microbial cell counting, wherein the apparatus comprises a DMD (Digital Micromirror Device) module, a transparent channel chip module, a light path module, a detection and analysis module and an installation supporting module; the DMD module, the transparent channel chip module, the light path module and the detection and analysis module are sequentially installed on the installation supporting module;
   the transparent channel chip module comprises a microchannel, and a width of the microchannel is adapted to a diameter of the cells in a liquid, so that the cells can circulate one by one in the microchannel;
   the DMD module comprises a DMD, and a turning direction of each micromirror in the DMD is adjustable; and
   when the apparatus is used to count the cells in the liquid, the liquid circulates through the microchannel in the transparent channel chip module, at the same time, detection light is used to irradiate the transparent channel chip module, the detection light passes through the transparent channel chip module in a forward direction and then irradiates the DMD module, is reflected by the DMD in the DMD module, then passes through the transparent channel chip module in a reverse direction, and then is adjusted by the light path module to reach the detection and analysis module, and the detection and analysis module calculates the number and size of the cells in the liquid according to a change of light intensity of the detection light.

2. The apparatus for microbial cell counting according to claim 1, wherein the transparent channel chip module comprises a microchannel plate made of a transparent material; the microchannel is a grooved with a rectangular cross section formed in the microchannel plate; and the microchannel plate is further provided with counterbores arranged corresponding to the DMD in the DMD module, the microchannel is communicated with all the counterbores, and the diameter of the counterbores is greater than the width of the microchannel.

3. The apparatus for microbial cell counting according to claim 2, wherein the DMD module further comprises a DMD control plate, and the DMD control plate is configured to control each micromirror in the DMD to turn in direction according to a predetermined rule.

4. The apparatus for microbial cell counting according to claim 2, wherein the cross section of the microchannel is square, the side length is 5-7 μm, and the diameter of the counterbores is 7-10 rim.

5. The apparatus for microbial cell counting according to claim 4, wherein the transparent channel chip module further comprises a chip fixing frame, a channel fixing frame and a channel cover sheet;
   the chip fixing frame is connected to the DMD module, and is configured to fix the microchannel plate above the DMD in the DMD module; a sinking through hole is formed in the center position of the chip fixing frame, and the microchannel plate, the channel cover sheet and the channel fixing frame are sequentially placed in the through hole;
   the channel fixing frame is configured to fix the channel cover sheet and the microchannel plate on the chip fixing frame; and
   the channel cover sheet is made of a transparent material, and is configured to cover the microchannel plate to prevent the liquid circulating in the microchannel from being contaminated.

6. The apparatus for microbial cell counting according to claim 5, wherein the transparent channel chip module further comprises two liquid pipelines and a pump; and the two liquid pipelines are respectively connected to an inlet and an outlet of the microchannel, wherein the other end of the liquid pipeline connected to the inlet of the microchannel is connected with the pump, and the pump is configured to inject liquid into the microchannel, so that the liquid circulates through the microchannel.

7. The apparatus for microbial cell counting according to claim 6, wherein the inlet and the outlet of the microchannel are respectively provided with a rectangular groove, and the size of the rectangular groove is 50 μm×50 μm×7 μm.

8. The apparatus for microbial cell counting according to claim 1, wherein the light path module comprises a detection light source, a beam splitter, a plano-concave lens, plano-convex lenses and a focusing objective lens; and the light path module is configured to ensure that the detection light emitted by the detection light source is amplified by one plano-convex lens and then vertically irradiates the transparent channel chip module through the beam splitter, passes through the transparent channel chip module in a forward direction and then irradiates the DMD module, is reflected by the DMD in the DMD module and then passes through the transparent channel chip module in a reverse direction, passes through the beam splitter, then sequentially passes through one plano-convex lens and the plano-concave lens to reach the focusing objective lens, and then is converged on a detection device in the detection and analysis module by the focusing objective lens.

9. The apparatus for microbial cell counting according to claim 1, wherein the detection and analysis module comprises a light detection device, a PC (Personal Computer) and analysis software; and the detection and analysis module is configured to obtain light intensity data of the detection light reaching the light detection device, and analyze a cell number and cell size distribution diagram through the analysis software according to the light intensity data.

10. A method of using the apparatus for microbial cell counting according to claim 1, and the method comprises:
    injecting a cell suspension into the microchannel, using detection light to irradiate the transparent channel chip module during the flow of the cell suspension in the microchannel; enabling the detection light to pass through the transparent channel chip module in a forward direction and then irradiate the DMD module, be reflected by the DMD in the DMD module and then pass through the transparent channel chip module in a reverse direction, and then be adjusted by the light path module to reach the detection and analysis module; calculating the number and size of the cells in the liquid by the detection and analysis module according to the light intensity change of the detection light; and enabling each micromirror in the DMD in the DMD module to turn in direction according to a certain rule during counting, so as to adjust the light intensity detected by the detection and analysis module.

11. The method according to claim 10, wherein the DMD module uses Discovery series of a DLP chip, and each micromirror in the DMD in the DMD module turns according to the rule set by the DLP chip.

12. The method according to claim 11, wherein the method comprises:

setting a flow rate of the cell suspension as v, a cross-sectional area of the microchannel as s, a sampling time as T, a sampling rate as C, and a difference between a current signal detected at the ith site at the time t and a reference current value as $\Delta I_i(t)$, wherein the reference current value is the current value when pure liquid flows through, and the ith site is the position on the microchannel corresponding to the ith micromirror in the DMD;

defining number of cells at a single sampling point at the ith site as:

$$P_i = n(I^*_{n+1} > \Delta I_i(t) \geq I^*_n)$$

wherein n is an integer, $I^*_i$ corresponds to reference value of the current value difference of i cells, cell concentration is $$C = \frac{c}{vsk} \sum_k P_i,$$

and k is number of detection sites; and letting $k_d$ represent cell diameter corresponding to the reference value of unit current difference, obtaining the cell diameter $$D_i(t) = k_d \frac{\Delta I_i(t)}{P_i}$$

sampled at the ith site at the time t, obtaining a mean value based on the cell diameter obtained at each site, and then drawing a cell size distribution diagram.

13. A computer device, comprising a memory, a processor and a computer program stored in the memory and capable of running on the processor, wherein when the processor performs the computer program, the steps of the method according to claim 10 are implemented.

* * * * *